United States Patent

Kohoot

(10) Patent No.: US 10,214,706 B2
(45) Date of Patent: Feb. 26, 2019

(54) FRAGRANCE CARRIER

(71) Applicant: Mark Kohoot, Pepper Pike, OH (US)

(72) Inventor: Mark Kohoot, Pepper Pike, OH (US)

(*) Notice: Subject to any disclaimer, the term of this patent is extended or adjusted under 35 U.S.C. 154(b) by 0 days.

(21) Appl. No.: 15/592,819

(22) Filed: May 11, 2017

(65) Prior Publication Data

US 2017/0327768 A1 Nov. 16, 2017

Related U.S. Application Data

(60) Provisional application No. 62/334,655, filed on May 11, 2016.

(51) Int. Cl.
| | | |
|---|---|---|
| *A61L 9/04* | (2006.01) | |
| *A61K 8/00* | (2006.01) | |
| *C11B 9/00* | (2006.01) | |
| *C07C 69/18* | (2006.01) | |
| *C08K 5/103* | (2006.01) | |
| *C07C 69/003* | (2006.01) | |
| *A61Q 13/00* | (2006.01) | |

(52) U.S. Cl.
CPC ............ *C11B 9/00* (2013.01); *A61Q 13/00* (2013.01); *C07C 69/003* (2013.01); *C07C 69/18* (2013.01); *C08K 5/103* (2013.01)

(58) Field of Classification Search
CPC ......... C11B 9/00; C07C 69/003; C07C 69/18; C08K 5/103

USPC ............................................. 512/4, 1
See application file for complete search history.

(56) References Cited

U.S. PATENT DOCUMENTS

| | | | | |
|---|---|---|---|---|
| 2005/0227906 A1* | 10/2005 | Schudel | ................ | A61K 8/11 512/2 |
| 2016/0032217 A1* | 2/2016 | Benoit | ................ | A61K 8/37 514/788 |

OTHER PUBLICATIONS

Ebsco, Final Report on the Safety Assessment of Triacetin, 2003, International Journal of Toxicology, 22, 1-10 (Year: 2003).*

* cited by examiner

*Primary Examiner* — Jessica Whiteley
(74) *Attorney, Agent, or Firm* — Baker & Hostetler LLP

(57) ABSTRACT

A novel fragrance carrier comprising 1,2,3-triacetoxypropane (triacetin) of formula I:

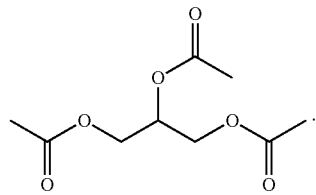

Formula I

5 Claims, No Drawings

FRAGRANCE CARRIER

CROSS REFERENCE TO RELATED APPLICATIONS

This application is a Non-provisional patent application and claims priority to U.S. Provisional Application Ser. No. 62/334,655, filed on May 11, 2016, titled "FRAGRANCE CARRIER", the disclosure of which is incorporated herein by reference in its entirety.

FIELD OF THE INVENTION

The present invention generally relates to a carrier for a fragrance or fragrance carrier. More particularly, the present invention pertains to a non-toxic carrier for a fragrance or fragrance carrier and a method of production thereof.

BACKGROUND OF THE INVENTION

It is generally known that carriers are presently utilized in the fragrance industry. Typically, these carriers are used to improve handling characteristics, facilitate dissolving the fragrance into a matrix, modify the dissipation of the fragrance, and/or modify the duration of a fragrance device. Examples of fragrance devices include such items as an air freshener, fragrance satchel, or aromatherapy device. Conventionally, fragrance carriers have included various alcohols such as ethanol, isopropyl, and methanol and oils that resist turning rancid such as jojoba, coconut, and sunflower oil. However, these traditional fragrance carriers may be prohibitively expensive, may adversely modify the dissipation of the fragrance (e.g., too fast or too slow), may have insufficient shelf life, and/or other such negative traits. In order to reduce these negative traits, conventional fragrance carriers now include synthetic molecules derived from petrochemicals. Unfortunately, some of these conventional carriers may have negative acute and/or chronic health implications.

Accordingly, it is desirable to provide an fragrance carrier having a similarity to lily of the valley that is capable of overcoming the disadvantages described herein at least to some extent.

SUMMARY OF THE INVENTION

The foregoing needs are met, to a great extent, by the present invention, wherein a carrier for a fragrance that is capable of overcoming the disadvantages described herein at least to some extent is provided.

An embodiment of the present invention pertains to a fragrance carrier having 1,2,3-triacetoxypropane (triacetin) of formula I:

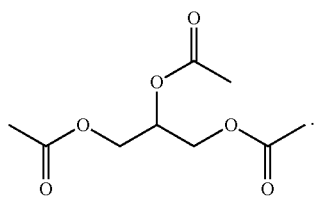

Formula I

Another embodiment of the present invention relates to a fragrance mixture having a fragrance carrier having 1,2,3-triacetoxypropane (triacetin) of formula I:

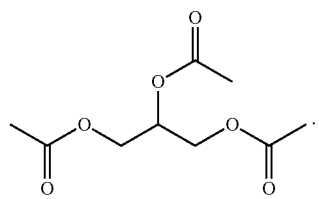

Formula I

Yet another embodiment of the present invention pertains to a fragrance device having a fragrance mixture having a fragrance carrier having 1,2,3-triacetoxypropane (triacetin), the fragrance device further comprising a polyamide-3 polymer and an essential oil.

Yet another embodiment of the present invention relates to a method of mixing a fragrance mixture. The method having the steps of melting a polyamide-3 polymer by heating until liquid, mixing 1,2,3-triacetoxypropane (triacetin) with the liquid polyamide-3, and mixing an essential oil into the polyamide-3/triacetin mixture.

There has thus been outlined, rather broadly, certain embodiments of the invention in order that the detailed description thereof may be better understood herein, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Embodiments of the invention provide a novel fragrance carrier, namely 1,2,3-triacetoxypropane which is more generally known as triacetin and glycerin triacetate and the novel fragrance carrier may include variations thereof. Other embodiments of the invention may provide novel fragrance mixtures that include the novel fragrance carrier. Yet other embodiments of the invention may provide methods of mixing the novel fragrance mixtures. In various embodiments of the invention, the novel fragrance carrier includes a compound of formula I:

Formula I

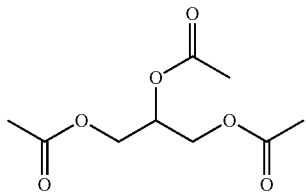

It is an advantage of one or more of the embodiments of the invention that the novel fragrance carrier is non-toxic. In this regard, triacetin has been considered as a possible source of food energy in artificial food regeneration systems on long space missions. Triacetin is believed to be safe to get over half of one's dietary energy from triacetin[1]. It is another advantage of one or more of the embodiments of the invention that fragrances are soluble in the novel fragrance carrier. Without being limited to any one or more of the following, the following list includes examples of suitable essential oils that are soluble in triacetin:

[1] Shapira, Jacob; Mandel, Adrian D.; Quattrone, Phillip D.; Bell, Nancie L. (1968). "Current Research On Regenerative Systems" Tokyo: Committee On Space Research, Eleventh Annual Meeting. Retrieved 2014 Jun. 20.

TABLE I

| Suitable essential oils |
|---|
| *Abies Balsamea* - Fir |
| *Acacia Dealbata* - Mimosa |
| *Achillea Millefolium* - Yarrow |
| *Alpinia Officinarum* - Galangal |
| *Amyris Balsamifera* - Amyris |
| *Anethum Graveolens* - Dill |
| *Angelica Archangelica* - Angelica |
| *Aniba Rosaeodora* - Rosewood |
| *Anthemis Nobilis* - Roman Chamomile |
| *Apium Graveolens* - Celery |
| *Artemisia Dracunculus* - Tarragon |
| *Balsamodendron Myrrha* - Myrrh |
| *Betula Alba* - Birch |
| *Boswellia Carteri* - Frankincense |
| *Bursera Delpechiana* - Linaloe |
| *Cananga Odorata* - Ylang Ylang |
| *Canarium Luzonicum* - Elemi |
| *Cedrus Atlantica* - Cedarwood Atlas |
| *Cinnamomum Camphora* - Camphor |
| *Cinnamomum Zeylanicum* - Cinnamon |
| *Cinnamomum Cassia* - Cassia |
| *Cistus Ladaniferus* - Labdanum |
| *Citrus Aurantifolia* - Lime |
| *Citrus Aurantium* - Neroli |
| *Citrus Aurantium* (Leaves) - Petitgrain |
| *Citrus Aurantium* aur. - Bitter Orange |
| *Citrus Bergamia* - Bergamot |
| *Citrus Cinensis* - Orange |
| *Citrus Cinensis* (Blossom) - Orange Blossom |
| *Citrus Junos* - Yuzu |
| *Citrus Limon* - Lemon |
| *Citrus Paradisii* - Grapefruit |
| *Citrus Reticulata* - Mandarin |
| *Coriandrum Sativum* - Coriander |
| *Crocus Sativus* - Saffron |
| *Cuminum Cyminum* - Cumin |
| *Cupressus Sempervirens* - Cypress |
| *Curcuma Longa* - Tumeric |
| *Cymbopogon Citratus* - Lemongrass |
| *Cymbopogon Martinii* - Palmarosa |
| *Cymbopogon Nardus* - Citronella |
| *Daucus Carota* - Carrot Seed |
| *Dianthus Caryophyllus* - Carnation |
| *Elettaria Cardamomum* - Cardamom |
| *Eucalyptus Globulus* - Eucalyptus |
| *Evernia Prunastri* - Oak Moss |
| *Ferula Galbaniflua* - Galbanum |

TABLE I-continued

| Suitable essential oils |
|---|
| *Foeniculum Vulgare* - Fennel |
| *Gardenia Grandiflora* - Gardenia |
| *Gaultheria Procumbens* - Wintergreen |
| *Helichrysum Angustifolium* - Helichrysum, Immortelle |
| *Humulus Lupulus* - Hop |
| *Hyacinthus Orientalis* - Hyacinth |
| *Hyssopus Officinalis* - Hyssop |
| *Illicium Verum* - Aniseed China Star |
| *Inula Graveolens* - Inula |
| *Jasminum Officinale* - Jasmine |
| *Juniperus Communis* - Juniper |
| *Juniperus Oxycedrus* - Cade |
| *Juniperus Virginiana* - Virginian Cedarwood |
| *Laurus Nobilis* - Laurel |
| *Lavandula Angustifolia* - Lavender |
| *Lavandula Latifolia* - Spike Lavender |
| *Leptospermum Scoparium* - Manuka |
| *Lindera Benzoin* - Benzoin |
| *Lippia Citriodora* - Lemon Verbena |
| *Lippia Javanica* - Zinziba |
| *Litsea Cubeba* - Litsea |
| *Lonicera Caprifolium* - Honeysuckle |
| *Matricaria Recutita* - German Chamomile |
| *Melaleuca Leucadendra* - Cajuput |
| *Melaleuca Alternifolia* - Tea Tree |
| *Melaleuca Viridiflora* - Niaouli |
| *Melissa Officinalis* - Melissa |
| *Mentha Piperita* - Peppermint |
| *Mentha Pulegium* - Pennyroyal |
| *Michelia Champaka* - Champaka |
| *Miroxylon Balsamum* - Peru Balsam |
| *Myrica Gale* - Bog Myrtle |
| *Myristica Fragrans* - Nutmeg |
| *Myrtus Communis* - Myrtle |
| *Nardostachys Jatamansi* - Spikenard |
| *Nelumbo Nucifera* - Lotus |
| *Ocimum Basilicum* - Basil |
| *Ocimum Sanctum* - Holy Basil |
| *Origana Majorana* - Sweet Majoram |
| *Ormenis Multicaulis* - Chamomile Maroc |
| *Osmanthus Fragrans* - Osmanthus |
| *Pelargonium Rosa* - Rose Geranium |
| *Perilla Frutescens* - Perilla |
| *Petroselinum Sativum* - Parsley |
| *Pimenta Racemosa* - Bay |
| *Pinus Sylvestris* - Pine |
| *Piper Nigrum* - Black Pepper |
| *Plumeria Rubra* - Frangipani |
| *Pogostemon Patchouli* - Patchouli |
| *Polianthes Tuberosa* - Tuberose |
| *Ravensara Aromatica* - Ravensara |
| *Rhododendron Anthopogon* - Rhododendron |
| *Rosa Damascena* - Rose |
| *Rosa Mochata* - Rose Musk |
| *Rosmarinus Officinalis* - Rosemary |
| *Salvia Officinalis* - Sage |
| *Salvia Sclarea* - Clary Sage |
| *Santalum Album* - Sandalwood Mysore |
| *Santalum Spicatum* - Australian Sandalwood |
| *Syzygium Aromaticum* - Clove |
| *Tagetes Glandulifera* - Tagetes or Marigold |
| *Tanacetum Vulgare* - Tansy or Wild Tansy |
| *Thymus Serpyllum* - Red Thyme |
| *Thymus Vulgaris* - Sweet (White) Thyme |
| *Tilia Cordata* - Linden Blossom |
| *Tsuga Canadensis* - Spruce |
| *Turnera Diffusa* - Damiana |
| *Valeriana Officinalis* - Valerian |
| *Vanilla Planifolia* - Vanilla |
| *Vetyveria Zizanoides* - Vetyver |
| *Viola Odorata* - Violet Leaf |
| *Zingiber Officinale* - Ginger |

It is yet another advantage of one or more of the embodiments of the invention that triacetin facilitates transporting of suitable fragrances through a polyamide polymer matrix. In this regard, a fragrance device such as an aroma therapy device, air freshener, or the like may be fabricated by forming a mixture of a polyamide resin, triacetin, and one or more fragrance. The fragrance mixture may be molded into a shape and/or placed in a container. It has been found that the fragrance transporting properties of triacetin are unexpectedly superior to conventional fragrance carriers. Examples of the unexpectedly superior fragrance transporting properties of triacetin include long lasting scent from the fragrance device, even production of scent from the fragrance device, and/or efficient transport of fragrance out of the fragrance device.

Suitable fragrance devices generally include aroma therapy devices, deodorants, air fresheners, and the like. Furthermore, it is within the purview of embodiments of the invention that the novel fragrance carrier described herein may be integrated into a perfume, a cologne, an eau du toilette, an eau du parfum, a hand sanitizer, a cosmetic, a personal care product, a cleansing product, a fabric softener, and the like.

In general, in addition to the novel fragrance carrier described herein, suitable fragrance mixtures and fragrance devices may include conventional ingredients such as, for example, solvents, other carriers, stabilizers, emulsifiers, moisturizers, dispersants, diluents, thickeners, thinners, adjuvants, and the like.

In the following examples, triacetin is incorporated into a fragrance mixture in a particular method. However, it is within the scope and spirit of the invention that triacetin is incorporated into a fragrance mixture and variations thereof in any suitable manner.

Methods

Example 1

Fabricating a Fragrance Device

Step 1: Melting a Polymer:
One part polyamide-3, volume to volume (v/v), is heated to 85° C. until liquid. Polyamide-3 is a polymer formed by the condensation of Dilinoleic Acid, ethylenediamine, polypropylene glycol diamine end-capped with PEG/PPG-32/10 aminopropyl methyl ether. One part triacetin v/v is added to the liquid polyamide-3 and mixed. The mixture is cooled to a range of about 67° C. to about 70° C.

Step 2: Incorporation of Fragrance:
One part essential oil fragrance v/v is added to the liquid mixture of polyamide-3 and triacetin in the temperature range of about 67° C. to about 70° C. and mixed in a sealed mixing vessel configured to re-incorporate volatilized elements of the essential oil fragrance back into the mixture. For example, the volatile components, being in a closed system, may form a condensate within the sealed mixing vessel and precipitate back into the mixture. In this manner, all of the components of the essential oil fragrance present in the natural or unprocessed state may be retained. The mixture is poured into a mold or cartridge. The mixture is cooled until gelled and, if molded, removed from the mold.

By cooling the liquid mixture of polyamide-3 and triacetin to the temperature range of about 67° C. to about 70° C., volatilization of the essential oil fragrance is minimized. In addition, at temperatures above 70° C., some components of the essential oil fragrance may react chemically or be otherwise altered which may degrade or otherwise alter the fragrance. Mixture of the essential oil fragrance in the liquid mixture of polyamide-3 and triacetin in the sealed mixing vessel further reduces volatilization of the essential oil fragrance. During mixing, the container temperature may be maintained to the range of about 67° C. to about 70° C. to maintain the fragrance mixture in the liquid state and facilitate pouring the fragrance mixture into the mold or cartridge.

Example 2

Fabricating a Fragrance Device

Step 1: Melting a Polymer:
Two parts polyamide-3 v/v is heated to 85° C. until liquid. One part triacetin v/v is added to the liquid polyamide-3 and mixed. The mixture is cooled to a range of about 67° C. to about 70° C.

Step 2: Incorporation of Fragrance:
One part essential oil fragrance v/v is added to the liquid mixture of polyamide-3 and triacetin in the temperature range of about 67° C. to about 70° C. and mixed in a sealed mixing vessel configured to re-incorporate volatilized elements of the essential oil fragrance back into the mixture. The mixture is poured into a mold or cartridge. The mixture is cooled until gelled and, if molded, removed from the mold. By using two parts polyamide-3, the resulting fragrance device may be relatively more firm as compared to the fragrance device of example 1. Depending upon the unit cost of polyamide-3, the materials cost of the fragrance device of example 2 may be relatively higher than the fragrance device of example 1.

Example 3

Fabricating a Fragrance Device

Step 1: Melting a Polymer:
One part polyamide-3 v/v is heated to 85° C. until liquid. Two parts triacetin v/v is added to the liquid polyamide-3 and mixed. The mixture is cooled to a range of about 67° C. to about 70° C.

Step 2: Incorporation of Fragrance:
One part essential oil fragrance v/v is added to the liquid mixture of polyamide-3 and triacetin in the temperature range of about 67° C. to about 70° C. and mixed in a sealed mixing vessel configured to re-incorporate volatilized elements of the essential oil fragrance back into the mixture. The mixture is poured into a mold or cartridge. The mixture is cooled until gelled and, if molded, removed from the mold. By using two parts triacetin, the resulting fragrance device may be relatively less expensive to manufacture as compared to the fragrance device of example 1. Of note, as the ratio of triacetin relative to polyamide-3 and essential oil fragrance increases beyond 1:1:1, or 33% v/v, the triacetin tends to flow out from the polymer matrix of the polyamide-3 which may result in a relatively shorter shelf life for some applications.

Example 4

Fabricating a Fragrance Device

Step 1: Melting a Polymer:
One part polyamide-3 v/v is heated to 85° C. until liquid. The liquid polyamide-3 is cooled to a range of about 67° C. to about 70° C.

Step 2: Incorporation of Fragrance:
One part essential oil fragrance v/v is added to the liquid polyamide-3 in the temperature range of about 67° C. to about 70° C. and mixed in a sealed mixing vessel configured to re-incorporate volatilized elements of the essential oil fragrance back into the mixture. The mixture is poured into a mold or cartridge. The mixture is cooled until gelled and, if molded, removed from the mold. By removing triacetin from the mixture, the resulting fragrance device may be relatively more expensive to manufacture as compared to the fragrance devices of examples 1-3. Removal of the triacetin may reduce the rate of fragrance release from the resulting fragrance device as compared to the fragrance devices of examples 1-3. As a consequence, removal of triacetin may not be suitable for some fragrance applications.

As is demonstrated in examples 1-4 described herein, the ratios of the various components of the fragrance device may be varied as suitable for the fragrance application.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A fragrance mixture comprising:
    a fragrance carrier comprising 1,2,3-triacetoxypropane (triacetin) of formula I:

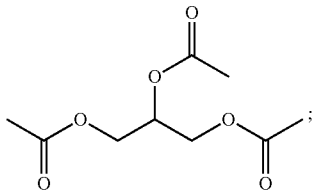

Formula I a Polyamide-3, wherein the 1,2,3-triacetoxypropane and the Polyamide-3 are added together at a 1:1 ratio v/v to form the fragrance mixture configured to melt in a temperature range of 67° C. to 70° C. and wherein the fragrance mixture configured to incorporate an essential oil fragrance at a 1:1 ratio v/v.

2. A method of mixing a fragrance mixture comprising the steps of:

melting a polyamide-3 polymer by heating until liquid;

mixing 1,2,3-triacetoxypropane (triacetin) with the liquid polyamide-3; and mixing an essential oil into the polyamide-3/triacetin mixture; wherein the ratio of the essential oil:polyamide-3:triacetin is 1:1:1 to form a mixture configured to melt in a temperature range of 67° C. to 70° C.

3. The method according to claim 2, further comprising the steps of:

heating the polyamide-3 polymer to 85° C. to liquefy the polyamide-3 polymer; and cooling the polyamide-3/triacetin mixture to a range of about 67° C. to about 70° C. before adding the essential oil.

4. The method according to claim 2, further comprising the step of mixing the essential oil into the polyamide-3/triacetin mixture in a closed container.

5. The method according to claim 2, further comprising the step of pouring the fragrance mixture into a mold or cartridge.

* * * * *